United States Patent [19]

Chupp

[11] Patent Number: 4,545,677

[45] Date of Patent: Oct. 8, 1985

[54] PRISMATIC BEAM EXPANDER FOR LIGHT BEAM SHAPING IN A FLOW CYTOMETRY APPARATUS

[75] Inventor: Vernon L. Chupp, Los Altos, Calif.

[73] Assignee: Becton, Dickinson and Company, Paramus, N.J.

[21] Appl. No.: 586,162

[22] Filed: Mar. 5, 1984

[51] Int. Cl.⁴ ............................................. G01N 33/48
[52] U.S. Cl. .................................... 356/39; 350/421; 356/71; 356/72
[58] Field of Search ............................. 356/39, 71, 72; 350/421

[56] References Cited

U.S. PATENT DOCUMENTS 3,826,364 7/1974 Bonner et al. ........................... 209/3
4,084,881 4/1978 Hirabayashi et al. ............... 350/421

Primary Examiner—Bernard D. Pianalto
Attorney, Agent, or Firm—Richard J. Rodrick

[57] ABSTRACT

A flow cytometry apparatus for determining characteristics of cells or the like flowing in a liquid stream includes a nozzle for generating a liquid flow path for moving cells therethrough substantially one at a time. A light source, such as a laser, provides a beam of illumination. At least one prism is interposed in the path of the incident beam of illumination for expanding the beam in at least one direction and for directing the expanded beam toward the cells in the flow path. A lens is provided to focus the expanded beam on the moving cells. An appropriate sensor detects light with respect to each moving cell for associating that detected light with a characteristic of such cell.

19 Claims, 4 Drawing Figures

PRISMATIC BEAM EXPANDER FOR LIGHT BEAM SHAPING IN A FLOW CYTOMETRY APPARATUS

BACKGROUND OF THE INVENTION

1. Field of the Invention

The present invention relates to a flow cytometry apparatus, and more particularly, concerns a flow cytometry apparatus for determining characteristics of cells or the like, which includes improved optics for focusing the light beam on the moving cells.

2. Description of the Prior Art

Flow cytometry apparatuses rely upon the flow of cells or other particles in a liquid flow stream in order to determine one or more characteristics of the cells under investigation. For example, a liquid sample containing cells is directed through the flow cytometry apparatus in a fast moving liquid stream so that each cell passes, substantially one at a time, through a sensing region. Changes in electrical impedance as each cell passes through the sensing region have been associated with the determination of cell volume. Similarly, if an incident beam of light is directed at the sensing region, the passing cells scatter such light as they pass therethrough. This scattered light has served as functions of cell shape, index of refraction, opacity, roughness and the like. Further, fluorescence emitted by tagged cells which have been excited as a result of passing through the excitation energy of the incident light beam is detectable for the identification of specifically marked cells. Not only is cell analysis performed on the flow cytometry apparatuses, but sorting of cells is also achieve. Lasers have been used as the source of the incident beam of illumination in flow cytometry apparatuses, as well as sources of incoherent light, such as mercury arc lamps.

In laser excited flow cytometry, in particular, a tightly focused laser beam is typically brought into coincidence with the cells or the like which are to be analyzed in conjunction with the light beam. Thus, the light beam allows the analysis to be conducted as a result of light scattered by the cells or fluorescence emitted thereby. As the cells travel in a normally vertical trajectory in their liquid flow path from the nozzle tip to the cell collector, they pass through the focused laser beam which normally travels on a substantially horizontal trajectory. The optical system, frequently multichannel, for measuring fluorescence or light scatter typically has a viewing axis which is mutually normal to both the liquid flow stream and the laser beam. Whenever the laser beam intercepts a cell, an optical pulse is generated, the intensity and wavelength profile of which characterizes the cell. Optical pulses are ultimately converted to digits and processed by a computer according to preselected operator functions. Output data is typically presented to the operator in conjunction with this digital information. Since it is desirable that the pulses provide intensity information about the cell rather than the laser beam, it is further desirable that the vertical dimension of the focused laser spot be reduced so as to be smaller than the typical cells under investigation.

Moreover, the electrical measuring system for analyzing the pulses is sometimes concerned with only the height of the pulses rather than the area. In this event, reduction of the vertical focal waist of the laser beam to that approaching the cell diameter causes an increase in the gathered signal in direct proportion thereto. On the other hand, reduction of the horizontal focal waist of the laser beam to less than the cell diameter usually leads to deleterious results by magnifying the uncertainty in the precise horizontal position of the liquid flow stream. In this event, poorer resolution results, which in this field of technology, is referred to as increased coefficient of variation. Accordingly, an improved illuminating system desirably would include a focal region with the vertical beam waist substantially smaller than the horizontal beam waist. Such asymmetric beam shaping is not uncommon in laser flow cytometry.

For instance, it is well understood that single mode continuous wave lasers of the type used in flow cytometry apparatuses have beam intensity profile functions which are Gaussian and that the following equation expresses the beam waist when focused with a lens:

$$\delta = (4\lambda f)/(\pi w)$$

Where, $\lambda$ is laser wavelength;
f is lens focal length;
w is width of the unfocused laser beam; and
$\delta$ is minimum focal waist as limited by diffraction.
(w and $\delta$ are usually dimensioned to the $1/\epsilon^2$ intensity points.

From the above equation it is evident that to reduce the beam waist, either the lens focal length (f) must be decreased or the unfocused laser beam width (w) must be increased or expanded. Of course, either approach is successful only so long as the angles are small enough so that geometric abberations are not a factor.

Currently, the most common way of producing a focused beam waist which is smaller in the vertical plane than the horizontal, relies upon cylindrical lenses. Typically, an elliptical beam shape can be created in which the vertical beam width is greater than the horizontal beam width, and then focusing can be achieved with a spherical lens having a specific focal length. Alternatively, it has been known to rely on a circular incident beam focused on the cell by asymmetric, usually cylindrical, focusing optics. The same Gaussian relationship pertains to this type of focusing optics. Any number of variations of these techniques may be used to create an asymmetric spot on the flowing cells in the liquid flow stream.

All of the known prior art systems have a chromatic problem when more than one laser is employed simultaneously as the source of excitation light, and when relying on one of the above-described cylindrical lens focusing approaches. Each of the cylindrical lenses focuses the different wavelength lasers at concomitantly different distances from the lens. Thus, where the flowing liquid stream of cells would intersect the first laser in a tightly focused zone, the cell would, a few microseconds later, intersect the second laser beam on a larger substantially defocused zone with a corresponding degradation in performance. If cylindrical lenses are used, rectification of this problem requires two or three complicated element lenses carefully designed with different glasses of appropriately varying dispersions. Usually, such combinations may correct chromatic abberation adequately over only a part of the required wavelength region. Furthermore, the axes of the individual cylindrical elements need to be carefully controlled. Even if the cylindrical lenses are carefully configured, they may contribute optical abberations which have to be kept within the diffraction limit at the cell space in order to produce a beam shape for optimum performance.

As a result of the foregoing deficiencies, there is clearly a need for improvement in light beam shaping for flow cytometry apparatuses in order to produce a focal region with the vertical beam waist substantially smaller than the horizontal beam waist. It is to such an improvement that the present invention is directed.

SUMMARY OF THE INVENTION

The flow cytometry apparatus of the present invention for determining characteristics of cells or the like flowing in a liquid stream comprises means for moving cells, substantially one at a time, in a liquid flow path. Means provides a beam of illumination. Prism means in the path of the incident beam of illumination expands the beam in at least one direction and directs the expanded beam toward the cells in the flow path. Means focuses the expanded beam on the moving cell. Means for detecting light with respect to each moving cell is included, which also associates the detected light with a characteristic of each cell.

In a preferred embodiment of the present invention, the prism means includes two refractive prisms interposed in the path of a light beam generated by a laser. The prisms are positioned so as to have an air gap therebetween and each prism includes an apex angle whose magnitude is such that the incidence angle of the laser beam is substantially near Brewster's angle. Each prism preferably has an exit surface oriented so as to be substantially normal to the path of the laser beam. Each prism has refractive capabilities for expanding the incident laser beam in a direction substantially parallel to the direction of the cell flow path. A focusing lens is provided to focus the beam at the liquid flow path so that the focal region has a vertical beam waist less than the horizontal beam waist.

In accordance with the principles of the present invention, light beam focusing is achieved without reliance on the presently known and used cylindrical focusing lenses. By relying on a prismatic refraction scheme, chromatic abberations are either eliminated or substantially reduced since the wavefront which is planar upon entering a prismatic surface, remains planar upon leaving such prismatic surface. In the present invention the only optical element that need be achromatic is a spherical sample focusing lens, which is easier to fabricate than a cylindrical lens. An additional advantage of the prismatic beam expander of the present invention is that, in some instances, the choice of incident angle and prism materials can be selected to approach Brewster's angle to thereby assure very high transmitting efficiency of the polarized laser beam without the need for multi-layer anti-reflection coatings. Another significantly advantageous feature is that the prismatic beam expander scheme of the present invention is readily adaptable for use with multiple light sources, such as lasers, which operate at different wavelengths, in the simultaneous analysis of cells flowing in the flow cytometry apparatus. Greater efficiency of operation of the optics of the system is also achieved.

BRIEF DESCRIPTION OF THE DRAWINGS

FIG. 1 is a schematic illustration of a preferred embodiment of the optical elements and light paths of a flow cytometry apparatus for determining characteristics of cells or the like;

DETAILED DESCRIPTION

Figure 1:
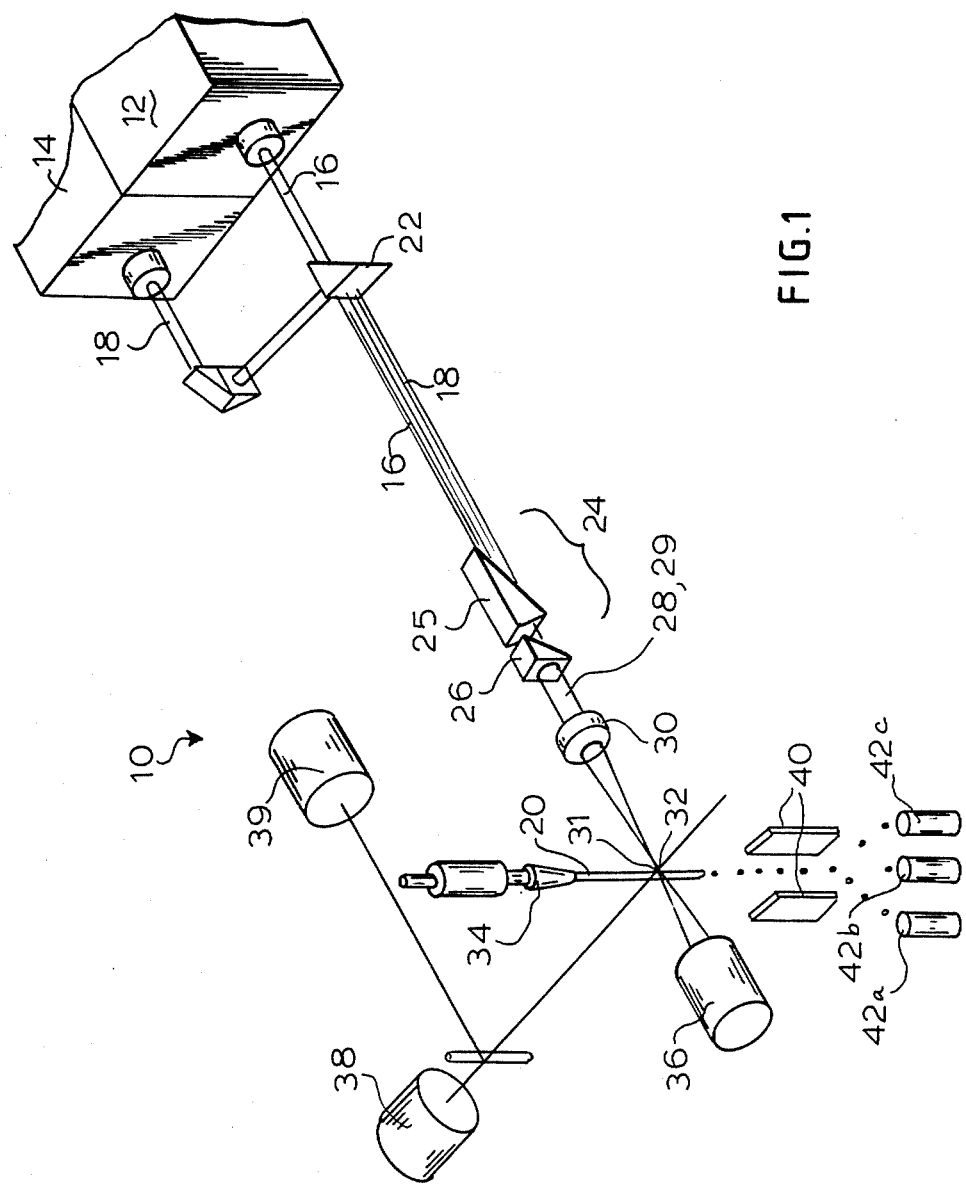

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, the optical and cell flow elements of a flow cytometry apparatus 10 are illustrated. The optical and flow elements of FIG. 1 represent the major components of a flow cytometry apparatus for moving particles, such as cells or the like, in a liquid stream, substantially one at a time, in order to assess those particles for specific characteristics thereof. For example, the elements of the device of FIG. 1 may be included in a FACS TM fluorescence-activated cell sorter, manufactured and sold by the FACS Systems Division of Becton, Dickinson and Company, Sunnyvale, Calif. The FACS cell sorter analyzes and separates cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry apparatuses, whether measuring light scatter, particle volume, fluorescence or other optical parameters for the identification or quantification of cells or the like in a sample liquid medium. The optical elements, in particular, of the present invention represent the essence of the improvement in flow cytometry apparatuses such as described in the aforementioned patent.

As illustrated in FIG. 1, light energy is provided for the present flow cytometry apparatus by two lasers 12 and 14. In this embodiment being described, two sources of light are provided in flow cytometry apparatus 10 so that it is possible to detect and quantify a plurality of different types of cells having different fluorescence, light scatter, volume or other detectable characteristics. It is understood, however, that the inclusion of two lasers in the embodiment illustrated in FIG. 1 is merely preferable and serves as an exemplary embodiment of employing more than one light energy source and analysis elements in the type of invention being described.

In the present invention, lasers 12 and 14 are selected to produce primary emissions of coherent light and specific wavelengths separated from each other in the spectral range. One such laser 12 useful for the present invention is an argon ion laser having a primary emission at 488 nm. Laser 14 is preferably selected to operate at a different, separated wavelength from laser 12. One such laser 14 which may be used in the present invention is a rhodamine 6-G dye laser which has a primary emission at 600 nm. Other lasers may also be utilized. Further, and although the present invention is most useful in focusing laser beams, non-laser light sources, such as mercury or xenon arc lamps may be used instead of laser illumination. If separated wavelength operation, however, is desired for the flow cytometry apparatus, the choice of light illumination would be lasers.

Laser beams 16 and 18 emerge from lasers 12 and 14, respectively. These emerging laser beams are unfocused, at this time, with respect to the cells flowing in the liquid flow stream 20. In the embodiment being described, laser 12 is positioned in substantially horizontal alignment with respect to flow stream 20 so that unfocused laser beam 16 is directed straight toward the liquid flow stream. On the other hand, unfocused laser beam 18 is directed through two directional prisms 21 and 22 so as to be in line with laser beam 16. However, although laser beams 16 and 18 travel toward the flowing cells on an axis substantially transverse to the direction of the flow path of cells, beam 18 is vertically displaced, downwardly, with respect to beam 16 as its emerges from turning prism 22. Both of the unfocused laser beams 16 and 18 are directed, in converging fashion, to a prismatic beam expander 24, represented, in the present embodiment by two prisms 25 and 26. Upon emerging from prismatic beam expander 24, the respective beams are expanded in the vertical direction, the expanded laser beams being designated by numerals 28 and 29, respectively, in FIG. 1. The expanded laser beams pass through a focusing lens 30 which focuses the laser beams in two regions 31 and 32 of liquid stream 20. Focal regions 31 and 32 are substantially vertically displaced from each other.

A nozzle 34, incorporated within the flow cytometry apparatus of the present invention, facilitates the flowing of cells within liquid stream 20. The utilization of a nozzle of this type is well-known and is described, for example, in U.S. Pat. No. 3,826,364. As each cell passes through regions 31 and 32, light scattered thereby may be detected by an appropriate photodetector 36. Similarly, fluorescence, if emitted by cells energized by the laser illumination, may be detected by fluorescence detectors 38 and 39. If the flow cytometry apparatus is intended to sort and collect cells having certain characteristics, charging plates 40 may be employed to collect cells in different containers 42a, b and c.

Figure 2:
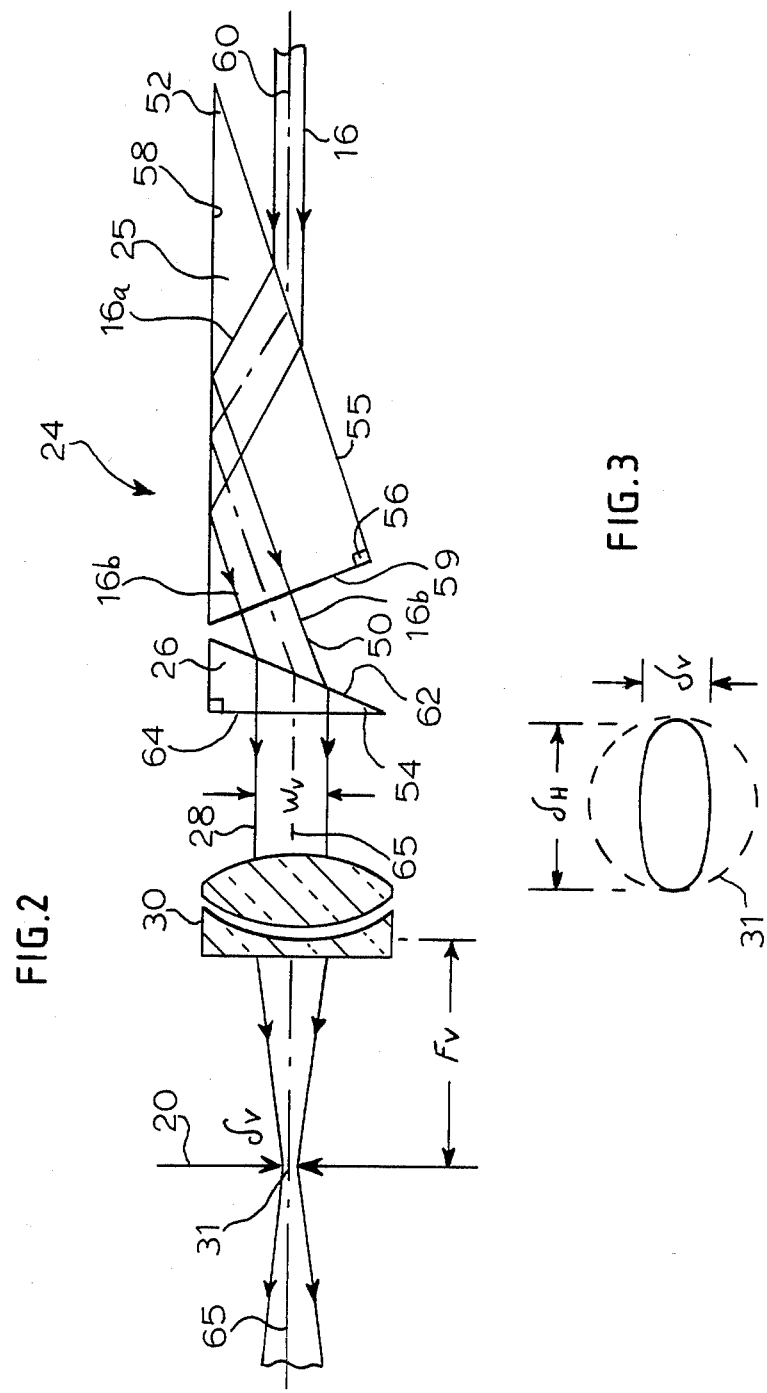
FIG. 2 is a schematic illustration of the optical elements of the apparatus of FIG. 1 depicting the expansion of the laser beam in the vertical direction.

Referring now to FIG. 2, a more detailed illustration of prismatic beam expander 24, along with its optical function, can be seen. For purposes of clarity, only the path of laser beam 16 is depicted in FIG. 2 so that the effect of beam expansion can be more clearly perceived. Both of prisms 25 and 26 are substantially right triangularly shaped refractive prisms interposed in the laser beam path. These prisms are closely spaced to each other, but an air gap 50 is located between the prisms, the purpose of which will be more clearly pointed out hereinafter. Each prism is further chosen so that its incidence angle is substantially at Brewster's angle. The apex angle of each prism has been designated by numerals 52 and 54, respectively. As is well known in the optical field, Brewster's angle represents the angle of incidence at which the amount of reflectance is minimized for light polarized parallel to the plane of incidence. Thus, at such angle of incidence, there would be little or no reflection losses. Brewster's angle is, moreover, a function of the prism material. As seen in FIG. 2, prism 25 is oriented so that surface 55 between apex angle 52 and the right angle 56 is incident to unfocused laser beam 16. Laser beam 16 travels toward surface 55 on an axis 60 which is substantially transverse to the direction of liquid flow stream 20. When light passes from a rare to a dense medium, such as from air into a prism, at a large angle of incidence, the light beam is bent as a result of the refractive properties of the prism. Further, after laser beam 16 is bent, as designated by numeral 16a, an expansion of the beam width results. Expanded beam 16a then strikes surface 58 which is an internal reflective surface. Accordingly, expanded beam 16a undergoes an internal reflection, designated as 16b. Laser beam 16b is also expanded with respect to incident beam 16. This expanded beam 16b exits prism 25 through exit surface 59; as seen in FIG. 2, expanded beam 16b travels through exit surface in a direction substantially normal thereto. Preferably, exist surface 59 may be coated with a layer of antireflectance material to improve the efficiency of transmission therethrough. Once expanded beam 16b passes out of prism 25, it enters air gap 50.

From air gap 50, expanded beam 16b once again passes from a rare to a dense medium as it strikes surface 62 of second prism 26. Light beam 16b is then bent inside prism 26 in a direction so that it exits substantially normal to exit surface 64. As in prism 25, the bending of beam 16b in prism 26 causes a further expansion in the vertical direction so that upon exiting prism 26 a significantly expanded beam 28 results. It is pointed out that prism 25 and 26 are positioned with their apex angles complementary to each other so that resulting expanded beam 28 travels on an axis 65 substantially parallel to and in alignment with original axis 60 of incident beam 16. Due to the orientation of prisms 25 and 26 laser beam 16 is expanded in only one direction, i.e., the vertical direction which is, in this embodiment, substantially parallel to the direction of liquid flow stream 20. Thus, expanded light beam 28, while expanded in the vertical direction, remains substantially constant with respect to the original width of the beam in the horizontal plane.

Figure 3:
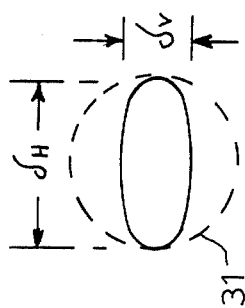
FIG. 3 is an enlarged plan view of the focused laser beam through which cells flow in the liquid stream illustrating the vertical beam waist being substantially smaller than the horizontal beam waist.

Expanded beam 28 passes through focusing lens 30 so that the beam can be focused in region 31 through which liquid flow stream 20 passes. Focal region 31 is illustrated in phantom in FIG. 3. It can be seen that the vertical beam waist, designated as $\delta_v$, is substantially smaller than the horizontal beam waist, designated as $\delta_h$. This is due to the fact that only the vertical component of the incident laser beam was expanded through the prisms. According to the Gaussian relationship set forth above, expansion or increase of the width of the unfocused laser beam will result in a diminution or decrease in the minimal focal waist in the plane where the unfocused laser width was increased. The elliptical shape of the focused laser beam in region 31 is such that $\delta_v$ is typically less than the diameter of the cells being analyzed, whereas $\delta_h$ is equal to or slightly larger than the diameter of cells under investigation. As a result of this elliptical arrangement of focused laser beam, optical signal intensity or pulse height is increased to thereby render the electronics of this apparatus more effective.

Figure 4:
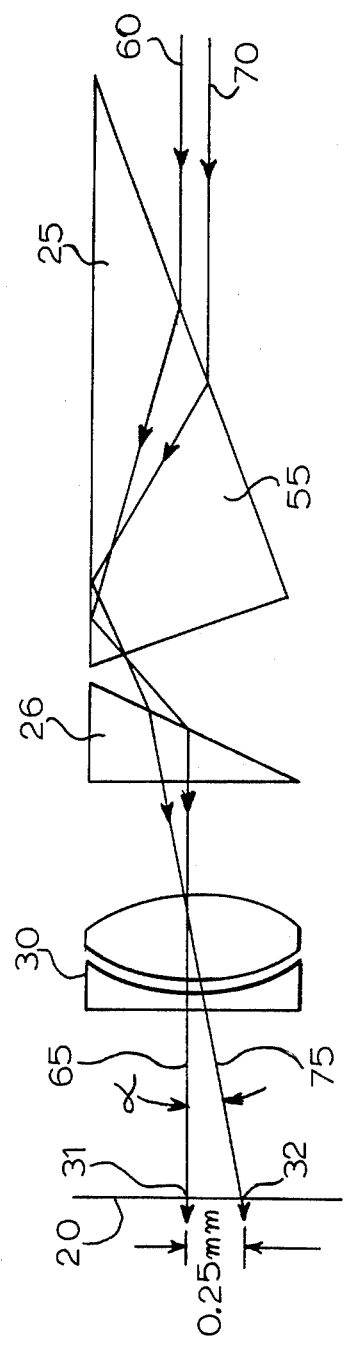
FIG. 4 is a schematic illustration of the optical elements of the flow cytometry apparatus of FIG. 1 depicting the axes of two simultaneous laser beams being focused on the cells flowing in the liquid flow stream.

Turning now to FIG. 4, the axes of both laser beams are illustrated as the respective light beams travel through the prisms. In FIG. 4, the expansion feature has not been illustrated so that the divergence characteristics of the two laser beams can be more clearly seen. It is understood that each laser beam is, however, expanded in the vertical direction as it travels though the prisms, in similar fashion to that described in conjunction with FIG. 2.

As described above, axis 60 of laser beam 16 is substantially transverse to the direction of liquid flow stream 20. Further, axis 65 of expanded beam 28 is substantially parallel to and aligned with axis 60 as a result of the orientation of prisms 25 and 26. The axis of unfocused laser beam 18 is represented by axis line 70. As mentioned above in conjunction with FIG. 1, unfocused laser beam 18 is vertically displaced with respect to unfocused laser beam 16. Accordingly, as seen in FIG. 4, axis 70, representative of laser beam 18, is vertically displaced with respect to axis 60, representing laser beam 16. Both axes converge toward each other as they strike surface 55 of first prism 25. After beam expansion occurs, axis 65 represents the expansion of laser beam 16, whereas axis 75 represents the axis of laser beam 18. Axis 65 remains substantially horizontal with respect to liquid flow stream 20 and intersects the liquid flow stream at focal region 31. On the other hand, axis 75 after passing through second prism 26 and focal lens 30, diverges at a relatively small angle with respect to axis 65. This angle will depend upon the vertical displacement desired between focal areas 31 and 32 of the respective focused laser beams. In the embodiment being described, region 32 of the second focused laser beam is typically 0.25 mm vertically displaced from region 31 of the first focused laser beam. Thus, axis 75 is maintained at a vertical downward trajectory of a relatively small angle upon exiting the prismatic beam expander and focusing lens. In order to maintain the displacement between respective focal regions, lens 30 may be a spherical achromatic lens which facilitates the focusing of the second laser beam at a different spot from the first focused laser beam.

It is appreciated that while two prisms have been described in conjunction with the preferred embodiment herein, the present invention is not limited to the use of two prisms. Thus, one prism or more than two prisms may be employed depending upon the structural layout of the optical elements of the flow cytometry apparatus.

While the prisms may be fabricated of various refractive materials, fused quartz (silicon dioxide) is the material of choice. Prisms of shapes other than right triangles are also within the purview of the present invention.

Thus, the present invention provides an improved flow cytometry apparatus, particularly useful with laser beam illumination, for shaping the focused laser beam for improved optical effiency. The present invention is thereby inherently free of chromatic aberration, eliminates the need for complicated cylindrical optics and may be designed for high efficiency optical transmission without the need for special coatings.

What is claimed is:

1. A flow cytometry apparatus for determining characteristics of cells or the like flowing in a liquid stream comprising:
    means for moving cells, substantially one at a time, in a liquid flow path;
    means for providing an incident beam of illumination;
    at least one prism interposed in the beam of illumination and having refractive capabilities to expand the beam in at least one direction as the beam exits said prism, said prism oriented so that the expanded beam is directed toward said cells on an axis substantially transverse to the direction of said flow path;
    means for focusing said expanded beam in a region of said flow path so that the vertical beam waist is less than the horizontal beam waist;
    means for detecting light associated with each moving cell as it passes through said focused beam of illumination; and
    means for using said detected light to determine characteristics of said cells.

2. The apparatus of claim 1 wherein said means for providing said beam illumination is a source of coherent light.

3. The apparatus of claim 2 wherein said source of coherent light is a laser.

4. The apparatus of claim 3 wherein said prism includes a first refractive incident surface positioned at an angle with respect to the beam of illumination.

5. The apparatus of claim 4 wherein said angled incident surface is capable of expanding the beam of illumination in a direction substantially parallel to the direction of said flow path.

6. The apparatus of claim 5 wherein said prism includes an internal reflective surface to reflect said expanded beam and an exit surface out of which said reflected, expanded beam exits said prism.

7. The apparatus of claim 6 wherein said exit surface is oriented so as to be substantially normal to the expanded beam.

8. The apparatus of claim 1 wherein two refractive prisms are interposed in the beam of illumination, said prisms having an air gap therebetween and including angled incident surfaces so that the expanded beam of illumination, as it exits the second prism, travels substantially parallel to the incident beam of illumination.

9. The apparatus of claim 8 wherein said prisms are right triangularly shaped.

10. The apparatus of claim 9 wherein the apex angles of said prisms are chosen so that the angle of incidence at each prism is substantially at Brewster's angle.

11. The apparatus of claim 10 wherein the first prism in the path of said beam of illumination is positioned so that the surface between the apex angle and the right angle is incident to said beam.

12. The apparatus of claim 11 wherein the prisms are made of silicon dioxide.

13. The apparatus of claim 3 which further includes means for providing a second incident beam of illumination directed into said prism so that it expands in at least the same one direction as said first expanded beam as said second beam exits said prism, said second expanded beam of illumination adapted to exit said prism at a diverging angle with respect to said first expanded beam.

14. The apparatus of claim 13 which further includes means for focusing the second expanded beam on the cells in said flow path at a region substantially vertically displaced from the intersection region of said flow path by said first focused beam.

15. The apparatus of claim 14 wherein the focusing means for said first and said second beams includes a spherical achromatic lens positioned between said prism and said flow path.

16. The apparatus of claim 1 wherein said means for detecting light includes a device for detecting light scattered by the cells passing through said focused beam of illumination.

17. The apparatus of claim 1 wherein said means for detecting light includes a device for detecting fluorescence emitted by the cells passing through said focused beam of illumination.

18. A flow cytometry apparatus for determining characteristics of cells or the like flowing in a liquid stream comprising:
   means for moving cells, substantially one at a time, in a liquid flow path;
   means for providing a beam of illumination;
   prism means in the path of said incident beam of illumination for expanding said beam in at least one direction and for directing said expanded beam toward said cells in said flow path;
   means for focusing said expanded beam in a region of said flow path so that the vertical beam waist is less than the horizontal beam waist; and
   means for detecting light with respect to each moving cell and for associating said detected light with characteristics of said cells.

19. A flow cytometry apparatus for detecting characteristics of cells or the like flowing in a liquid stream comprising:
   means for moving cells, substantially one at a time, in a liquid flow path;
   a pair of lasers for providing two beams of unfocused illumination at different wavelengths;
   two right triangularly shaped prisms interposed in the path of both laser beams and having an air gap therebetween, the apex angles of said prisms chosen so that the angle of incidence at each prism is substantially at Brewster's angle and the exit surface of one of said prisms is substantially normal to the path of one of said beams, said prisms having refractive capabilities for expanding the incident laser beams in a direction substantially parallel to the direction of said cell flow path, said prisms oriented so that one of said expanded beams exits therefrom in a path substantially parallel to the path of its incident laser beam, said expanded beams adapted to exit said prisms at a diverging angle with respect to the vertical axis and to be directed toward said cells on an axis substantially transverse to the direction of said flow path;
   a focusing lens to focus said first expanded beam at a first region in said flow path and to focus said second expanded beam at a second region in said flow path substantially vertically displaced from said first region, each focal region having a vertical beam waist less than its horizontal beam waist;
   means for detecting light associated with each moving cell as it passes through said focused beams of illumination; and
   means for using said detected light to determine characteristics of said cells.

* * * * *